(12) United States Patent
Yamashita et al.

(10) Patent No.: US 6,437,182 B1
(45) Date of Patent: Aug. 20, 2002

(54) PROCESS FOR THE PREPARATION OF SORBIC ACID

(75) Inventors: Akira Yamashita; Mitsuhiro Kouno, both of Arai (JP)

(73) Assignee: Daicel Chemical Industries, Ltd., Osaka (JP)

( * ) Notice: Subject to any disclaimer, the term of this patent is extended or adjusted under 35 U.S.C. 154(b) by 0 days.

(21) Appl. No.: 09/555,094

(22) PCT Filed: Sep. 21, 1999

(86) PCT No.: PCT/JP99/05123

§ 371 (c)(1),
(2), (4) Date: May 24, 2000

(87) PCT Pub. No.: WO00/17145

PCT Pub. Date: Mar. 30, 2000

(30) Foreign Application Priority Data

Sep. 24, 1998 (JP) .......................................... 10-288795

(51) Int. Cl.[7] .............................................. C07C 57/10
(52) U.S. Cl. ....................................................... 562/601
(58) Field of Search ......................................... 562/601

(56) References Cited

U.S. PATENT DOCUMENTS 3,992,442 A * 11/1976 Kageyama et al.
4,296,243 A * 10/1981 Sato

FOREIGN PATENT DOCUMENTS

| JP | A-60188346 | 9/1985 |
|---|---|---|
| JP | A-9227447 | 9/1997 |

* cited by examiner

Primary Examiner—Paul J. Killos
Assistant Examiner—Zachary Tucker
(74) Attorney, Agent, or Firm—Birch, Stewart, Kolasch & Birch, LLP

(57) ABSTRACT

The invented process produces sorbic acid by hydrolysis of a polyester in the presence of an acid, which polyester is obtained from ketene and crotonaldehyde. The process includes the step of subjecting a decomposition reaction mixture of the polyester to solid-liquid separation at temperatures ranging from 30° C. to 60° C. to yield sorbic acid as a solid. The process may further include the step of rinsing the sorbic acid obtained by solid-liquid separation with an aqueous solution containing sorbic acid, which aqueous solution is formed in a purification process of sorbic acid subsequent to the solid-liquid separation.

The invented process can easily and efficiently remove tar substances by-produced in the reaction and can mitigate loads on a purification process.

15 Claims, No Drawings

PROCESS FOR THE PREPARATION OF SORBIC ACID

This application is the national phase under 35 U.S.C. §371 of PCT International Application No. PCT/JP99/05123 which has an International filing date of Sep. 21, 1999,which designated the United States of America.

TECHNICAL FIELD

The present invention relates to a process for producing sorbic acid which is useful as, for example, food additives. Particularly, the invention relates to a process for producing sorbic acid by decomposition of a polyester obtained from ketene and crotonaldehyde.

BACKGROUND ART

As processes for the commercial production of sorbic acid, processes are known which include the step of hydrolyzing a polyester in the presence of an acid, which polyester is obtained by a reaction of ketene with crotonaldehyde. For example, Japanese Examined Patent Application Publication No. 44-26646 discloses a process for producing sorbic acid. The process includes the steps of reacting ketene with crotonaldehyde in the presence of a catalyst to yield a reaction mixture, heating the reaction mixture under reduced pressure to remove unreacted crotonaldehyde and by-products of the reaction by distillation to yield a polyester containing the catalyst, decomposing the polyester with hydrochloric acid to yield a reaction mixture, and cooling the reaction mixture to yield sorbic acid.

In such processes for producing sorbic acid by hydrolyzing the polyester with an acid, a purified sorbic acid is generally obtained by preparing a reaction mixture slurry by the hydrolysis of the polyester in the presence of an acid, subjecting the reaction mixture slurry to filtration or another solid-liquid separation operation to yield a crude sorbic acid as a solid, and subjecting the crude sorbic acid to a purification process such as treatment with active carbon or crystallization. The reaction mixture slurry contains tar substances by-produced in the reaction. In the solid-liquid separation, some of the tar substances migrate to liquid portions, but others adhere to a surface of sorbic acid and migrate to solid portions. To obtain a highly purified sorbic acid having a satisfactory hue, loads on the subsequent purification process such as treatment with active carbon must be increased or a combination of several complicated purification processes must be employed.

The Japanese Examined Patent Application Publication No. 44-26646 discloses a process for producing sorbic acid. The process includes the steps of preparing a polyester from ketene and crotonaldehyde, and decomposing the polyester with hydrochloric acid having a concentration of 35% by weight or more at temperatures ranging from room temperature to around the boiling point of the hydrochloric acid used. In an example described in this publication, a crystalline sorbic acid is obtained by cooling a reaction mixture, separating a crude sorbic acid by filtration, washing the crude sorbic acid with water, putting the washed crude sorbic acid into water, heating and dissolving the mixture to yield a solution, adding activated carbon to the solution, boiling the mixture, and filtering the mixture while heating, and gradually cooling the resulting filtrate to yield a crystalline sorbic acid. Japanese Unexamined Patent Application Publication No. 9-227447 discloses a process for producing sorbic acid. The process includes the step of performing isomerization at a specific temperature after the completion of heat generation in the hydrolysis of the polyester. In an example described in this publication, a crude sorbic acid is obtained by cooling a reaction mixture to 25° C. and filtrating the cooled reaction mixture under suction. Japanese Unexamined Patent Application Publication No. 10-95745 discloses a process for producing sorbic acid, including the step of hydrolyzing the polyester with a mineral acid in the presence of a saturated fatty acid. An example shown in this publication describes that a crude sorbic acid was obtained by cooling a reaction mixture to 20° C. and filtrating the cooled reaction mixture under suction.

However, when a hydrolysis reaction mixture of the polyester is cooled to about 20° C. to 25° C. and is then filtered as in the above processes, such by-product tar substances are highly viscous, and large portions of the tar substances adhere to sorbic acid and migrate to solid portions. This markedly increases loads on subsequent sorbic acid purification process such as treatment with active carbon.

Such a decomposition reaction mixture of the polyester contains an acid used in the reaction. The acid will corrode apparatus and instruments in the purification process and should be preferably removed completely as soon as possible.

DISCLOSURE OF INVENTION

Accordingly, an object of the invention is to provide a process for producing sorbic acid, which is capable of easily and efficiently removing tar substances by-produced in a reaction and is capable of mitigating loads on a purification process.

Another object of the invention is to provide a process for efficiently producing a highly purified sorbic acid having a satisfactory hue.

It is a further object of the invention to provide a process for producing sorbic acid, which is capable of efficiently removing not only tar substances but also the acid used in a reaction.

The present inventors made intensive investigations to achieve the above objects, and found that tar substances can be efficiently removed by subjecting a decomposition reaction mixture of the polyester to solid-liquid separation at temperatures in a specific range.

Specifically, the invention provides a process for producing sorbic acid by hydrolysis of a polyester in the presence of an acid, which polyester is obtained from ketene and crotonaldehyde. The process includes the step of subjecting a reaction mixture formed by decomposition of the polyester to solid-liquid separation at temperatures ranging from 30° C. to 60° C. to yield sorbic acid as a solid.

BEST MODE FOR CARRYING OUT THE INVENTION

According to the invention, a polyester obtained from ketene and crotonaldehyde is hydrolized in the presence of an acid to yield sorbic acid. The polyester is generally shown by the following formula (1):

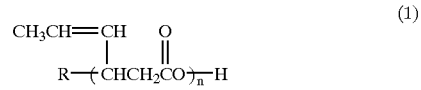

In the above formula, R is an acetoxy group or a hydroxyl group, and n denotes an integer of 2 or more (e.g., about 3 to 40).

The polyester can be obtained by conventional or known processes. For example, the polyester is obtained by reacting ketene with crotonaldehyde in the presence of a catalyst and in the absence of or in the presence of an inert solvent. Such catalysts include, but are not limited to, simple substances or compounds of manganese, cobalt, nickel, zinc, cadmium, and other transition metals; and pyridine, picoline, and other nitrogen-containing basic compounds. Examples of the compounds of the transition metals are oxides; salts of acetic acid, salts of isobutyric acid, salts of isovaleric acid, and salts of other organic acids; salts of sulfuric acid, salts of nitric acid, and salts of other inorganic acids; chlorides and other halides; acetylacetone complex salts, and other complex salts and complexes. Each of these catalysts can be used alone or in combination. The amount of the catalyst differs according to the type of the catalyst, but is generally about 0.1 to 10% by weight relative to the weight of ketene.

The reaction of ketene with crotonaldehyde is performed at a temperature of, for example, about 20° C. to 100° C., and preferably about 25° C. to 80° C.

A reaction mixture containing the polyester obtained through the reaction of ketene with crotonaldehyde is usually distilled to remove unreacted crotonaldehyde and low boiling impurities, and is then subjected to a hydrolysis reaction with an acid.

Acids for use in hydrolysis of the polyester include mineral acids such as hydrochloric acid and sulfuric acid. The hydrolysis of the polyester is frequently performed in hydrochloric acid. When the polyester is hydrolyzed with hydrochloric acid, the concentration of hydrochloric acid is, for example, about 15 to 40% by weight and more preferably about 23 to 36% by weight. An extremely low concentration of hydrochloric acid may invite a decreased reaction rate, and in contrast, an extremely high concentration of hydrochloric acid may invite disadvantages in handling property or ease of operation. The amount of hydrochloric acid in terms of hydrogen chloride is, for example, about 10 to 160 parts by weight, and preferably about 15 to 100 parts by weight relative to 100 parts by weight of the polyester. The hydrolysis reaction is performed at temperatures of, for example, about 10° C. to 110° C., and preferably about 50° C. to 100° C. An extremely low reaction temperature may decrease a reaction efficiency, and in contrast, an extremely high reaction temperature may increase by-production of tar substances and other impurities.

A reaction mixture obtained through hydrolysis of the polyester with an acid is usually a slurry containing sorbic acid dispersed in water. The reaction mixture contains, in addition to the sorbic acid and the acid used, tar substances and other impurities by-produced in the reaction. The reaction mixture is diluted or concentrated according to necessity, and is then subjected to solid-liquid separation to yield sorbic acid as a solid. Such solid-liquid separation means include, for example, filtration and centrifugal separation. In the invention, solid-liquid separation by filtration is preferred for ease of operation.

The invention has a main feature in that the solid-liquid separation operation is performed while controlling the temperature of the decomposition reaction mixture of the polyester to a range from 30° C. to 60° C., and preferably from 40° C. to 50° C. If the temperature of the reaction mixture during solid-liquid separation is less than 30° C., the tar substances are highly viscous, and large portions of the tar substances in the reaction mixture adhere to a surface of the sorbic acid and migrate to solid portions. A crude sorbic acid thus obtained has a markedly deteriorated hue. If the temperature exceeds 60° C., the solubility of sorbic acid to hydrochloric acid increases and the sorbic acid tends to migrate to a mother liquor to thereby increase loss. In addition, apparatus and instruments used in solid-liquid separation are liable to be corroded. In contrast, the invention performs solid-liquid separation under the specific temperature condition, and the formed tar substances are less viscous and are less adherent to sorbic acid. Most of the tar substances can migrate to the mother liquor in solid-liquid separation operation, and a crude sorbic acid less colored can be obtained. The sorbic acid does not have a significantly high solubility to the mother liquor, and a loss on separation of the sorbic acid is low. In addition, corrosion of apparatus and instruments by the acid for use in decomposition of the polyester can be minimized.

After the solid-liquid separation operation, the separated solid matter may be rinsed. The rinsing treatment can reliably remove trace acid and impurities attached to sorbic acid. In this case, the solid matter is preferably rinsed with an aqueous solution containing sorbic acid which is formed in a sorbic acid purification process after the solid-liquid separation process. Typically, an aqueous solution containing sorbic acid in a proportion of 0.1% by weight to saturation is advantageously used as the rinsing liquid. The use of an aqueous solution containing sorbic acid obtained in a subsequent process as a rinsing liquid can reduce loss of sorbic acid induced by dissolution, as compared with rinsing of the solid matter with water. In addition and advantageously, a discharge liquid from the process can be effectively used. The aqueous solution containing sorbic acid includes, for example, a filtrate of washings obtained by treating the crude sorbic acid obtained in the solid-liquid separation operation with active carbon, crystallizing and filtering the treated crude sorbic acid to yield a crystalline sorbic acid, and washing the crystalline sorbic acid with water.

A highly purified sorbic acid having a satisfactory hue can be obtained by subjecting the crude sorbic acid obtained by the solid-liquid separation operation to a conventional separation and purification means. Such separation and purification means include, for example, treatment with active carbon, crystallization, filtration, centrifugal separation, distillation, and recrystallization. The crude sorbic acid obtained by the invented process is significantly less colored and contains minimized tar substances attached thereto, and can greatly mitigate loads on the purification process and can simplify the purification process to thereby efficiently yield a high quality sorbic acid.

The product sorbic acid and its salts can be used as preservatives for foods such as fish pastes, butters, cheeses, bean pastes, and jams.

The invention subjects a decomposition reaction mixture of the polyester to solid-liquid separation under the specific temperature condition and can easily and efficiently remove tar substances by-produced in the reaction while avoiding loss of the sorbic acid. The crude sorbic acid thus obtained by solid-liquid separation contains markedly reduced amounts of tar substances and is significantly less colored, and can greatly mitigate loads on the purification process without requiring a significantly complicated purification process. The invention can therefore efficiently produce a highly purified sorbic acid having a satisfactory hue.

When the sorbic acid obtained by solid-liquid separation is rinsed with a sorbic acid-containing aqueous solution formed in a sorbic acid purification process subsequent to the solid-liquid separation operation, not only the tar substances but also the acid used in the reaction can be efficiently removed.

The present invention will now be illustrated in further detail with reference to several inventive examples and a comparative example below, which are not intended to limit the scope of the invention. All "parts" are by weight unless otherwise specified.

EXAMPLE 1

To 600 parts of crotonaldehyde, 2 parts of zinc isobutyrate was added as a catalyst, and 170 parts of a ketene gas was introduced at a temperature of 30° C. to 40° C. to perform a reaction. After completion of the reaction, excess crotonaldehyde was removed by distillation under reduced pressure to yield a highly viscous polyester. The yield of the polyester was 77% on the basis of ketene.

To 135 parts of the above-prepared polyester, 110 parts of a concentrated hydrochloric acid having a concentration of 34% by weight was added, and the resulting mixture was heated to 80° C. to decompose the polyester to thereby yield a crude sorbic acid slurry. The crude sorbic acid slurry was cooled to 45° C. and was then filtered under reduced pressure. A crude sorbic acid (residue) remained on a filter paper was analyzed and was found to have a moisture content of 20% by weight, and after drying, was found to have a tar content of 4% by weight and a hydrochloric acid content of 1.2% by weight. The residue was then rinsed under reduced pressure with pure water two times by weight that of the residue. As a result, the rinsed crude sorbic acid had a moisture content of 20% by weight, and a dried crude sorbic acid had a tar content of 3% by weight and a hydrochloric acid content of 0.4% by weight. The crude sorbic acid had a light brown color.

A sodium hydroxide aqueous solution was added to 125 parts of the obtained crude sorbic acid to yield a sodium sorbate aqueous solution. To this aqueous solution, 6 parts of active carbon was added and the resulting mixture was stirred for 30 minutes. The resulting mixture was then filtered to remove the active carbon, and a neutralization amount of a concentrated hydrochloric acid was added to the filtrate, and the mixture was cooled to precipitate sorbic acid. The precipitated sorbic acid was separated by filtration, was washed with water and was dried in vacuo to yield 106 parts of a purified sorbic acid.

EXAMPLE 2

The synthesis and decomposition of a polyester, and the filtration and rinsing of a decomposition reaction mixture of the polyester were performed in the same manner as in Example 1, except that a filtrate of washings was used, instead of pure water, as the rinsing liquid in the rinsing operation of the crude sorbic acid. The filtrate of washings was obtained by treating the crude sorbic acid with active carbon, crystallizing the treated crude sorbic acid to yield sorbic acid, washing the sorbic acid with water and filtrating washings, as in Example 1.

As a result, the crude sorbic acid after rinsing had a moisture content of 20% by weight, and a dried crude sorbic acid had a tar content of 3% by weight and a hydrochloric acid content of 0.4% by weight. The prepared crude sorbic acid had a light brown color.

COMPARATIVE EXAMPLE 1

The synthesis and decomposition of a polyester, and the filtration and rinsing of a decomposition reaction mixture of the polyester were performed in the same manner as in Example 1, except that the crude sorbic acid slurry obtained by decomposition of the polyester was cooled to 25° C. and was then filtered under reduced pressure.

As a result, before rinsing, the crude sorbic acid had a moisture content of 20% by weight, and a dried crude sorbic acid had a tar content of 6.5% by weight and a hydrochloric acid content of 1.2% by weight. After rinsing, the crude sorbic acid had a moisture content of 20% by weight, and a dried crude sorbic acid had a tar content of 6% by weight and a hydrochloric acid content of 0.4% by weight. The prepared crude sorbic acid had a dark brown color.

What is claimed is:

1. In a process for producing sorbic acid by hydrolysis of a polyester in the presence of an acid, said polyester being obtained from ketene and crotonaldehyde, wherein the improvement comprises:

subjecting a decomposition reaction mixture of said polyester to solid-liquid separation at temperatures ranging from 30° C. to 60° C. to yield sorbic acid as a solid.

2. The process according to claim 1, further comprising rinsing the sorbic acid obtained by solid-liquid separation with an aqueous solution containing sorbic acid, said aqueous solution being formed in a purification process of sorbic acid subsequent to said solid-liquid separation.

3. The process according to claim 1, wherein the polyester has the following formula:

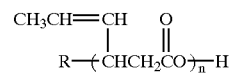

where R is an acetoxy or a hydroxyl group, and n is an integer of 2 or more.

4. The process according to claim 1, wherein the polyester is formed by the ketene and the crotonaldehyde in the presence of a catalyst.

5. The process according to claim 4, wherein the catalyst is a compound containing a nitrogen containing compound or a metal selected from the group consisting of manganese, cobalt, nickel, zinc, and cadmium.

6. The process according to claim 4, wherein the catalyst is a compound containing a metal selected from the group consisting of manganese, cobalt, nickel, zinc, and cadmium, and the metal is present as an oxide, a salt of an organic acid, a salt of an inorganic acid, a halide, a complex salt or a complex.

7. The process according to claim 4, wherein the catalyst is about 0.1 to 10% by weight relative to the weight of ketene.

8. The process according to claim 4, wherein the catalyst is zinc isobutyrate.

9. The process according to claim 2, wherein the aqueous solution contains sorbic acid in a proportion of about 0.1% by weight to saturation.

10. The process according to claim 2, wherein the aqueous solution is a filtrate of washings obtained by treating the sorbic acid obtained in the solid-liquid separation.

11. The process according to claim 10, wherein treating the sorbic acid comprises:

preparing an aqueous sorbate solution;

adding activated carbon to the sorbate solution;

filtering to remove the activated carbon;

precipitating sorbic acid;

filtering the precipitated sorbic acid; and washing the filtered sorbic acid with water.

12. The process according to claim 11, wherein the aqueous sorbate solution is prepared with aqueous sodium hydroxide.

13. The process according to claim 11, wherein precipitating the sorbic acid comprises:

neutralizing the sorbate solution; and cooling.

14. The process according to claim 13, wherein the neutralizing is performed using hydrochloric acid.

15. The process according to claim 14, wherein the hydrochloric acid is concentrated hydrochloric acid.

* * * * *